US006325063B1

(12) United States Patent
Volgyesi

(10) Patent No.: US 6,325,063 B1
(45) Date of Patent: Dec. 4, 2001

(54) BREATH-POWERED MIST INHALER

(76) Inventor: George A. Volgyesi, 36 Gatehead Road, Willowdale, Ontario (CA), M2J 2P5

( * ) Notice: Subject to any disclaimer, the term of this patent is extended or adjusted under 35 U.S.C. 154(b) by 0 days.

(21) Appl. No.: 09/233,913

(22) Filed: Jan. 21, 1999

(30) Foreign Application Priority Data

Jan. 26, 1998 (CA) .................................................. 2228182

(51) Int. Cl.$^7$ ...................................................... A61M 15/00
(52) U.S. Cl. ................................. 128/204.13; 128/203.12
(58) Field of Search .......................... 128/200.11, 200.12, 128/200.13, 200.14, 200.21, 200.24, 203.12, 203.23, 204.13, 204.14, 204.24, 204.25

(56) References Cited

U.S. PATENT DOCUMENTS 351,744 * 11/1886 Cushman ........................ 128/200.12
413,100 * 10/1889 Smith .............................. 128/200.12
418,813 * 1/1890 McQuigg ........................ 128/200.12
544,340 * 8/1895 Wright ............................ 128/200.12
813,425 * 2/1906 Hill ................................ 128/200.12
957,548 * 5/1910 Doane ............................ 128/203.24
5,655,517 * 8/1997 Coffee ............................ 128/203.12
5,727,546 * 3/1998 Clark et al. ..................... 128/203.24

* cited by examiner

*Primary Examiner*—Glenn K. Dawson
(74) *Attorney, Agent, or Firm*—Riches, McKenzie & Herbert

(57) ABSTRACT

A breath-powered inhalation device includes a hollow cylindrical body having an air inlet at one end and an air outlet at another end. The air outlet is narrowed so that air velocity increases as air moves through the outlet. At the air outlet is positioned a releasing mechanism which preferably has a fibre tip impregnated with a medicament or the like. As the air rushes past the releasing mechanism, the medicament or the like is atomized and carried into the respiratory tract of the user by the air. The breath-powered inhalation device of the present invention provides advantages over conventional inhalation devices using compressed gases as propellants since it is more compact, simpler and does not require synchronization of activation of the device and inhalation by the user.

9 Claims, 2 Drawing Sheets

BREATH-POWERED MIST INHALER

FIELD OF THE INVENTION

This invention relates to devices for administering medicaments or the like by inhalation.

BACKGROUND OF THE INVENTION

Conventional devices for administering a medicament or the like in the form of an aerosol or powder typically comprise atomizers or nebulizers. The medicaments contained in such devices are typically in admixture with a propellant such that, when a release valve in the device is opened, the propellant and medicament are forced out of the device in the form of a mist.

Such devices containing propellants are disadvantageous in that they typically provide a small number of doses, are fairly bulky, and require the user of the device to synchronize his or her inhalation with the opening of the release valve.

SUMMARY OF THE INVENTION

To overcome the above disadvantages of conventional inhalation devices, the present invention provides a breath-powered mist inhaler in which the force required to atomize or nebulize the medicament is provided by inhalation of the person using the device.

In one aspect, the present invention provides a breath-powered device for inhalation of a substance, comprising a hollow body having a first end and a second end and having a continuous air passage extending from the first end to the second end; an air inlet provided at the first end of the hollow body; an air outlet provided at the second end of the hollow body, the air passage decreasing in size between the air inlet and the air outlet; storage means for storing the substance; and a releasing mechanism from which the substance is released into the air passage, the releasing mechanism being impregnated with the substance and being located in the air passage proximate the air outlet.

Therefore, it is an object of the present invention to provide a breath-powered inhalation device.

BRIEF DESCRIPTION OF THE DRAWINGS

Further aspects and advantages of the present invention will become apparent from the following description, taken together with the accompanying drawings, in which.

DETAILED DESCRIPTION OF PREFERRED EMBODIMENTS

FIGS. 1 to 4 illustrate a preferred breath-powered inhalation device according to the present invention.

Figure 1:
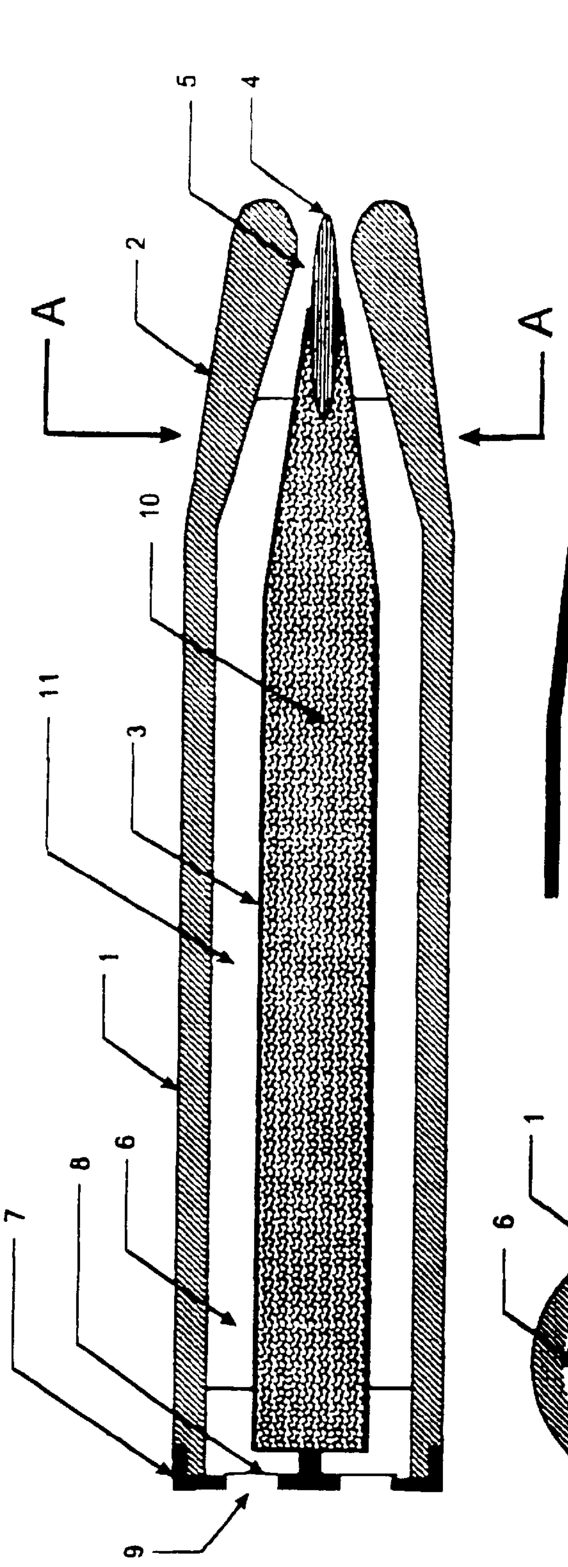
FIG. 1 is a cross-sectional view along a longitudinal axis showing a preferred breath-powered inhalation device according to the present invention.

The breath-powered inhalation device shown in FIG. 1 comprises a hollow body 1, one end of which is provided with an air inlet 9 and the other end of which is provided with an air outlet 5. The hollow body forms a continuous air passage 11 extending from the air inlet 9 to the air outlet 5.

As shown in FIG. 1, hollow body 1 is preferably of a generally cylindrical shape and is preferably of similar size as a pen or the like. Preferably, hollow body 1 has a length of about 12 to about 16 cm, and an outside diameter of from about 1 to about 3 cm. When not in use, air outlet 5 is preferably closed by protecting cap 12, preferably having a pocket clip 13 which allows the device to be carried in a shirt pocket. The hollow cylindrical body 1, protecting cap 12 and pocket clip 13 are preferably made from metal or plastic.

The hollow body 1 preferably has a generally cylindrical interior which decreases in diameter between air inlet 9 and air outlet 5, as shown in FIG. 1. Preferably, the inside diameter of hollow body 1 near air inlet 9 is from about 1 to about 3 cm. At the narrowest part of air outlet 5, the inside diameter of hollow body 1 is preferably from about 0.2 to about 0.5 cm. Therefore, when air is moved from air inlet 9 to air outlet 5, its velocity increases as the diameter of the air passage 11 decreases. The air achieves its highest velocity at the narrowest portion of the air outlet 5.

Figure 2:
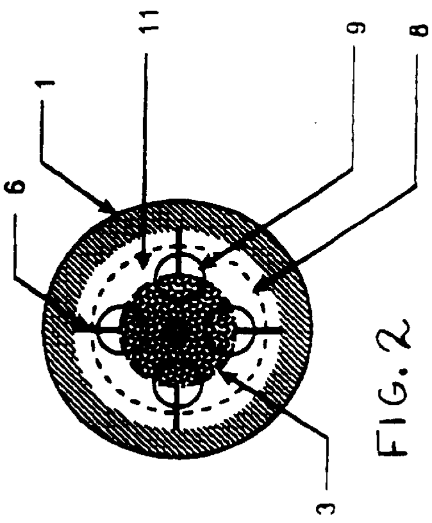
FIG. 2 is a cross-sectional view along a traverse axis of the breath-powered inhalation device shown in FIG. 1.
Figure 3:
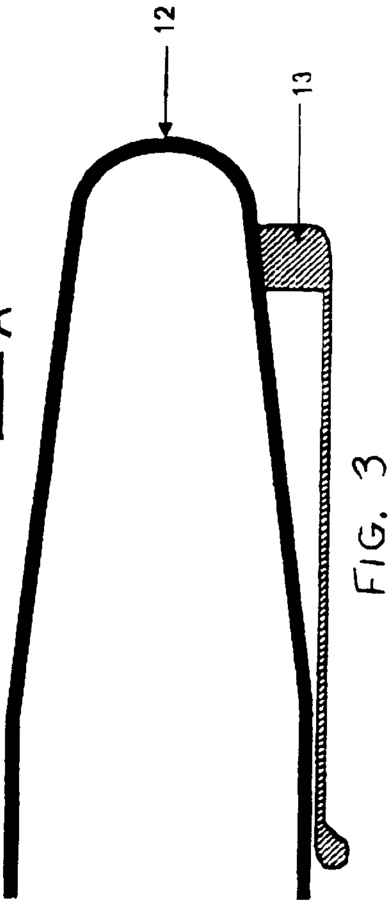
FIG. 3 is a cross-sectional view along a longitudinal axis showing a protecting cap for the breath-powered inhalation device of FIG. 1.

As shown in FIG. 2, air inlet 9 preferably comprises a plurality of holes through which air enters hollow body 1. The air inlet 9 is preferably also provided with a one-way valve 8 which permits air to enter hollow body 1 but does not permit air to exit hollow body 1 through the air inlet 9. Preferably, the one-way valve 8 comprises a one-way flap valve which is preferably made from rubber or plastic.

The breath-powered mist inhaler according to the present invention is preferably used to deliver a medicament or the like to the respiratory tract of the user of the device. The device preferably disperses a liquid containing the medicament or the like into air flowing through the device so that the medicament or the like is effectively atomized or nebulized into the form of an aerosol with liquid droplets containing the medicament or the like being carried into the respiratory tract of the user by the air moving through air passage 11 of the device.

As shown in FIG. 1, the breath-powered inhalation device also comprises a storage reservoir 3 in which the medicament or the like is stored. The storage reservoir 3 is preferably generally cylindrical in shape and is preferably radially centred in the hollow body 1 such that the air passage 11 is annular. The distance between the outside of storage reservoir 3 and the inner wall of hollow body 1 in the vicinity of air inlet 9 is preferably from about 0.2 to about 0.4 cm. As shown in FIG. 1, storage reservoir 3 preferably extends substantially the entire length of hollow body 1 to store a large number of doses of the medicament or the like.

The storage reservoir 3 is preferably tapered so as to have a decreased diameter in the vicinity of the air outlet 5. Further, the taper of the reservoir 3 is preferably such that air passage 11 is constricted in the vicinity of air outlet 5. Preferably, the distance between the outer surface of reservoir 3 and the inner wall of hollow body 1 in the vicinity of air outlet 5 is reduced to from about 4 to about 1.0 mm.

The storage reservoir 3 is preferably comprised of metal, glass or plastic and may preferably be removed from hollow body 1 and replaced so that the breath-powered inhalation device of the present invention may be reused. Preferably, as shown in FIG. 2, storage reservoir 3 is supported in its radially centred position by support fins 6 which, as shown in FIG. 1, extend along substantially the entire length of storage reservoir 3.

In addition, a screw cap 7 is preferably provided at the air inlet end of hollow body 1. When screw cap 7 is removed, storage reservoir 3 is removable from hollow body 1.

Furthermore, as shown in FIG. 1, the air inlet comprising the one-way flap valve 8 is preferably integrally formed with storage reservoir 3 and support ribs 6, so that these elements may be removed and replaced as a single unit.

Preferably, the storage reservoir 3 is filled with a fibrous material which is impregnated with the medicament or the like. Most preferably, the medicament or the like is in the form of a liquid, for example a solution or suspension, and the fibrous material preferably comprises glass or plastic micro-fibres in which the liquid medicament or the like is evenly distributed.

Figure 4:
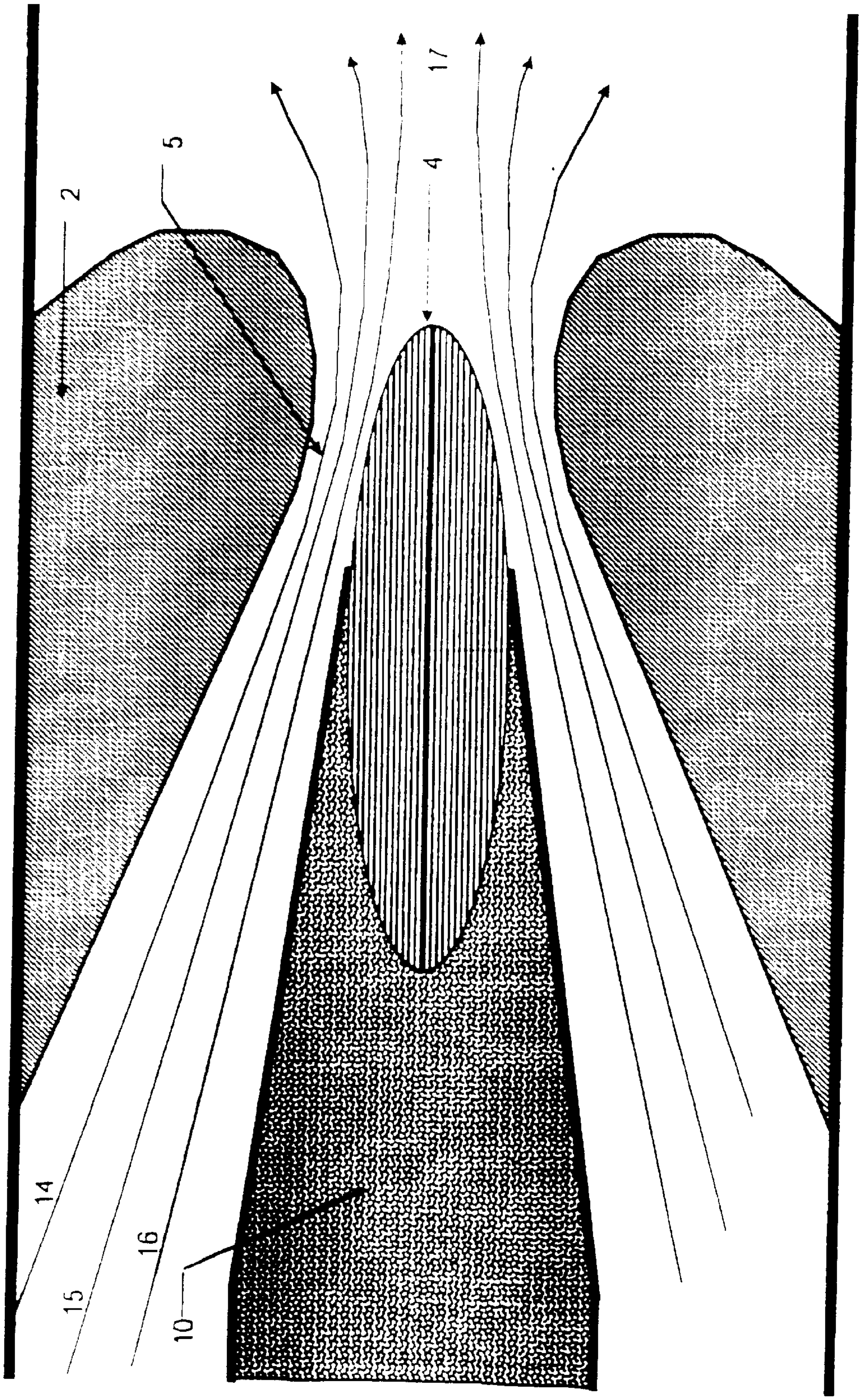
FIG. 4 is a close up view of the air outlet of the breath-powered inhalation device shown in the cross-sectional view of FIG. 1.

As most clearly shown in the close up of FIG. 4, the tapered end of preferred storage reservoir 3 has an open end from which projects a releasing mechanism 4 which is impregnated with the medicament or the like and is located in the air passage 11 proximate the air outlet 5.

Preferably, the releasing mechanism 4 comprises a fibre tip comprising a fibrous material containing multiple capillaries, and may preferably be the same or a different material as the fibrous material contained in the storage reservoir 3. The tip 4 draws the medicament or the like from the impregnated micro-fibres in the storage reservoir by capillary action, and the liquid medicament or the like is continually replaced at the fibre tip from the storage reservoir 3.

As shown in FIG. 4, fibre tip 4 is preferably radially centred in the outlet 5 of hollow body 1 so that all surfaces of fibre tip 4 are exposed to air passage 11. Air passage 11 is preferably at its narrowest point between fibre tip 4 and the inner wall of hollow body 1 at the air outlet 5, preferably being from about 0.2 to about 2.0 mm.

The operation of the preferred breath-powered inhalation device of the present invention is now described below with reference to the drawings.

After removing protective cap 12, the user places the air outlet end 5 of hollow body 1 into his or her mouth or nostril and inhales through the device. During inhalation, air enters through intake holes of the air inlet 9 and through the one-way valve 8. This air travels through air passage 11 from the air inlet 9 toward the air outlet 5. As the diameter of the air passage 11 decreases, the velocity of the air travelling through hollow body 1 increases. The air achieves its highest velocity at the narrowest portion of the air outlet. This is represented in FIG. 4 by streamlines 14, 15 and 16 of air. The closer the streamlines are to each other, the higher the velocity of the air.

The fibre tip 4 impregnated with the liquid medicament is positioned at this area of highest velocity, and when the air rushes past fibre tip 4, the liquid medicament held in the fibre tip 4 by capillary action is atomized by the Bernoulli effect from the ends of the capillaries contained in fibre tip 4. The air then carries the atomized liquid into the respiratory tract of the user. The active ingredient of the mist thus inhaled by the user reaches all parts of the airways and lungs where it may enter the blood stream and be transported to various organs, for example the brain.

The distribution of the mist in the respiratory tract is determined mainly by the size of droplets comprising the atomized mist. The droplet size can be controlled to a certain extent by the mean diameter of the capillaries in the fibre tip 4 and by the velocity of the air rushing past tip 4. The smaller the droplets, the deeper in the airway they will reach. The larger droplets "rain out" in the upper airway and only the very small droplets reach the alveoli in the lungs. By careful design, the desired proportion of the liquid can be made to reach each part of the airways.

Therefore, the present invention provides a highly compact and effective breath-powered inhalation device in which the storage reservoir containing the medicament or the like can be replaced, no moving parts are included, no batteries or compressed gases are required for activation, and no training is required to synchronize activation of the device and inhalation. The mist is delivered during the entire inhalation process and ceases to be delivered when inhalation stops.

Although the invention has been described in connection with certain preferred embodiments, it is not intended to be limited thereto. Rather, it is intended that the invention covers all alternate embodiments as may be within the scope of the following claims. The invention also includes all embodiments which are functional equivalents of the specific embodiments and features which have been described herein.

It will be further understood that, although various features of the invention have been described with reference to one or another of the embodiments of the invention, the various features and embodiments of the invention may be combined or used in conjunction with other features and embodiments of the invention as described herein.

What is claimed is:

1. A breath-powered device for inhalation of a substance comprising:

a hollow body having a first end and a second end and having a continuous air passage extending from the first end to the second end;

air inlet means provided at the first end of the hollow body;

air outlet means provided at the second end of the hollow body, the air passage decreasing in size between the air inlet means and the air outlet means;

storage means for storing the substance, wherein said storage means comprises a receptacle containing a fibrous material impregnated with the substance;

releasing means from which the substance is released into the air passage, the releasing means being impregnated with the substance and being located in the air passage proximate the air outlet means, wherein the releasing means comprises a fibre tip comprised of a fibrous material containing a plurality of capillaries, and wherein the fibre tip is in contact with the fibrous material inside the storage means, such that the fibre tip withdraws the substance from the fibrous material in the storage means by capillary action.

2. The breath-powered device of claim 1, wherein the storage means is located inside the hollow body.

3. The breath-powered device of claim 1, wherein the fibrous material is comprised of glass or plastic micro-fibres.

4. The breath-powered device of claim 3, wherein the hollow body has a cylindrical interior which decreases in diameter between the inlet means and the outlet means.

5. The breath-powered device of claim 4, wherein the storage means is cylindrical and is radially centred in the hollow body such that the air passage is annular.

6. The breath-powered device of claim 1, wherein the outlet means comprises a narrow opening in the second end of the hollow body, and wherein the fibre tip of the releasing means is radially centred in the narrow opening with ends of the plurality of capillaries communicating with the air passage in the narrow opening.

7. The breath-powered device of any one of claims 1, 2, 3, 4, 5 or 6, wherein the air inlet means comprises a one-way valve.

8. The breath-powered device of claim 1, wherein the substance is a medicament.

9. The breath-powered device of claim 8, wherein the medicament is stored in the storage means as a liquid.

* * * * *